(12) United States Patent  
Mou et al.

(10) Patent No.: US 11,391,708 B2  
(45) Date of Patent: *Jul. 19, 2022

(54) ACTUATING AND SENSING MODULE

(71) Applicant: Microjet Technology Co., Ltd., Hsinchu (TW)

(72) Inventors: Hao-Jan Mou, Hsinchu (TW); Ta-Wei Hsueh, Hsinchu (TW); Li-Pang Mo, Hsinchu (TW); Shih-Chang Chen, Hsinchu (TW); Ching-Sung Lin, Hsinchu (TW); Yung-Lung Han, Hsinchu (TW); Chi-Feng Huang, Hsinchu (TW); Chang-Yen Tsai, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 774 days.

This patent is subject to a terminal disclaimer.

(21) Appl. No.: 16/054,100

(22) Filed: Aug. 3, 2018

(65) Prior Publication Data

US 2019/0064104 A1 Feb. 28, 2019

(30) Foreign Application Priority Data

Aug. 22, 2017 (TW) .................................. 106128417

(51) Int. Cl.
  *F15B 15/20* (2006.01)
  *F16K 31/44* (2006.01)
  (Continued)

(52) U.S. Cl.
  CPC ...... *G01N 33/0009* (2013.01); *B01L 3/50273* (2013.01); *B01L 3/502715* (2013.01);
  (Continued)

(58) Field of Classification Search
  CPC ...... F04B 43/046; G01N 1/2273; G01N 1/24; G01N 27/407; G01N 33/0009;
  (Continued)

(56) References Cited

U.S. PATENT DOCUMENTS 3,266,293 A * 8/1966 Hubner .................. G01N 27/18  
  73/23.2  
2005/0170520 A1 * 8/2005 Schur .................... G01N 1/2273  
  436/149

(Continued)

FOREIGN PATENT DOCUMENTS

CN 103838900 A 5/2014  
CN 205030637 U 2/2016  
(Continued)

OTHER PUBLICATIONS

Guoping Xiong et al., A Review of Graphene-Based Electrochemical Microsupercapacitors, Electroanalysis, vol. 26, No. 1, Nov. 15, 2014, pp. 30-51 (Year: 2014).*

(Continued)

*Primary Examiner* — Marrit Eyassu  
(74) *Attorney, Agent, or Firm* — Birch, Stewart, Kolasch & Birch, LLP (57) ABSTRACT

An actuating and sensing module is provided. The actuating and sensing module includes at least one sensor, at least one actuating device and a power storage member. The sensor is disposed for measuring fluid. The actuating device is disposed proximate to the sensor and is disposed for transporting the fluid. The power storage member is configured as a graphene battery and is disposed for providing power to the at least one sensor and the at least one actuating device for driving the at least one sensor and the at least one actuating (Continued)

device. The actuating device is driven to transport the fluid toward the sensor so as to make the fluid measured by the sensor.

16 Claims, 10 Drawing Sheets

(51) Int. Cl.
| | | |
|---|---|---|
| G01D 11/24 | (2006.01) | |
| G01N 27/407 | (2006.01) | |
| G01N 33/00 | (2006.01) | |
| H01L 41/09 | (2006.01) | |
| G01N 1/22 | (2006.01) | |
| B01L 3/00 | (2006.01) | |
| F04B 43/04 | (2006.01) | |
| G01N 1/24 | (2006.01) | |

(52) U.S. Cl.
CPC ............ *F04B 43/046* (2013.01); *F15B 15/20* (2013.01); *F16K 31/44* (2013.01); *G01D 11/245* (2013.01); *G01N 1/2273* (2013.01); *G01N 1/24* (2013.01); *G01N 27/407* (2013.01); *H01L 41/09* (2013.01); *B01L 2300/023* (2013.01); *B01L 2300/0663* (2013.01); *B01L 2400/0439* (2013.01); *F15B 2015/208* (2013.01)

(58) Field of Classification Search
CPC .......... B01L 3/502715; B01L 3/50273; B01L 2300/023; B01L 2400/0439; B01L 2300/0663; F15B 15/20; F15B 2015/208; F16K 31/44; G01D 11/245; H01L 41/09
USPC ........................................................ 73/24.01
See application file for complete search history.

(56) References Cited

U.S. PATENT DOCUMENTS

| | | | | |
|---|---|---|---|---|
| 2008/0229805 | A1* | 9/2008 | Barket | G01N 1/2214 73/31.01 |
| 2010/0229658 | A1* | 9/2010 | Glezer | G01N 1/2273 73/863.81 |
| 2013/0223979 | A1* | 8/2013 | Locke | F04B 49/065 415/1 |
| 2014/0134053 | A1* | 5/2014 | Mayer | G01N 33/0009 422/83 |
| 2014/0178220 | A1* | 6/2014 | Fujisaki | F04B 45/047 417/413.2 |
| 2016/0186240 | A1* | 6/2016 | Andreyev | B01L 3/5029 435/287.2 |
| 2016/0223490 | A1 | 8/2016 | Astley et al. | |
| 2016/0282151 | A1* | 9/2016 | Kursula | G01N 33/0044 |
| 2016/0290912 | A1* | 10/2016 | Kent | G01N 15/1475 |
| 2016/0305415 | A1* | 10/2016 | Qureshi | G01N 1/2273 |

FOREIGN PATENT DOCUMENTS

| | | |
|---|---|---|
| CN | 205538890 U | 8/2016 |
| CN | 206038594 U | 3/2017 |
| EP | 3190421 A1 | 7/2017 |
| EP | 3203079 A1 | 8/2017 |
| TW | M525446 U | 7/2016 |
| TW | 201643425 A | 12/2016 |
| TW | M540931 U | 5/2017 |
| WO | WO 2016/182437 A1 | 11/2016 |

OTHER PUBLICATIONS

Extended European Search Report for European Application No. 18187198.9, dated Oct. 24, 2018.

Lin et al., "Integrated Microfluidics/Electrochemical Sensor System for Monitoring of Environmental Exposures to Lead and Chlorophenols," Biomedical Microdevices, vol. 3, No. 4, Jan. 1, 2001, pp. 331-338.

Xiong et al., "A Review of Graphene-Based Electrochemical Microsupercapacitors," Electroanalysis, vol. 26, No. 1, Nov. 15, 2014, pp. 30-51.

* cited by examiner

ACTUATING AND SENSING MODULE

FIELD OF THE INVENTION

The present disclosure relates to an electronic device, and more particularly to an actuating and sensing module applicable to an electronic device for monitoring environment.

BACKGROUND OF THE INVENTION

Nowadays, people pay much attention to the air quality in the environment. For example, it is important to monitor carbon monoxide, carbon dioxide, volatile organic compounds (VOC), fine suspended particle (PM2.5), and so on. The exposure of these substances in the environment will cause human health problems or even harm the life. Therefore, it is important for every country to develop and implement the environmental monitoring technology.

As known, portable electronic devices are widely used and applied in the modern lives. In other words, it is feasible to use the portable electronic device to monitor the environmental air. If the portable electronic device is capable of immediately providing people with monitored information relating to the environment for caution, it may help people escape or prevent from the injuries and influence on human health caused by the exposure of substances described above in the environment. In other words, the portable electronic device is suitably used for monitoring the environmental air.

Although it is obviously beneficial to make the portable electronic device equipped with sensor for monitoring the environmental air, however, when the sensor is integrated into the electronic device, the measuring sensitivity and the measuring precision should be taken into consideration. For example, when the sensor measures a nature air circulation, the sensor may fail to fetch a consistent airflow to maintain a stable measuring. Since it is difficult for the nature air circulation to trigger response action of the sensor, the response time of the sensor is prolonged and the object of real-time monitoring is negatively affected.

Therefore, there is a need to provide a technology for increasing the measuring accuracy of the sensor and decreasing the response time of the sensor.

SUMMARY OF THE INVENTION

An object of the present disclosure provides an actuating and sensing module including at least one sensor, at least one actuating device and a power storage member, which are integrated as a modularized structure. The actuating device is disposed for increasing the flow rate of fluid and providing an amount of fluid stably and uniformly. Since the sensor is provided with the amount of the fluid stably and uniformly, the response time of the sensor to the fluid is largely reduced and the measuring precision is increased.

Another object of the present disclosure provides an actuating and sensing module for monitoring the environment, thereby providing a portable device capable of monitoring the air quality. In other words, the actuating and sensing module can monitor the air quality outside of the filtering mask and transmit an output data of measured information to a connection device. The output data is displayed, stored and transmitted by the connection device. Consequently, the purpose of immediately displaying the output data and issuing a notification signal are achieved. Moreover, the output data can be transmitted to a cloud database. Consequently, the purpose of constructing and managing the cloud database can be achieved. Accordingly, an air quality notification mechanism and an air quality processing mechanism are enabled. Therefore, a user can wear an air-filtering protection device immediately to prevent from the influence on human health caused by the air pollution.

In accordance with an aspect of the present disclosure, an actuating and sensing module is provided. The actuating and sensing module includes at least one sensor, at least one actuating device and a power storage member. The sensor is disposed for measuring fluid. The actuating device is disposed proximate to the sensor and is disposed for transporting the fluid. The power storage member is configured as a graphene battery, and is disposed for providing power to the at least one sensor and the at least one actuating device for driving the at least one sensor and the at least one actuating device. The actuating device is driven to transport the fluid toward the sensor so as to make the fluid measured by the sensor.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
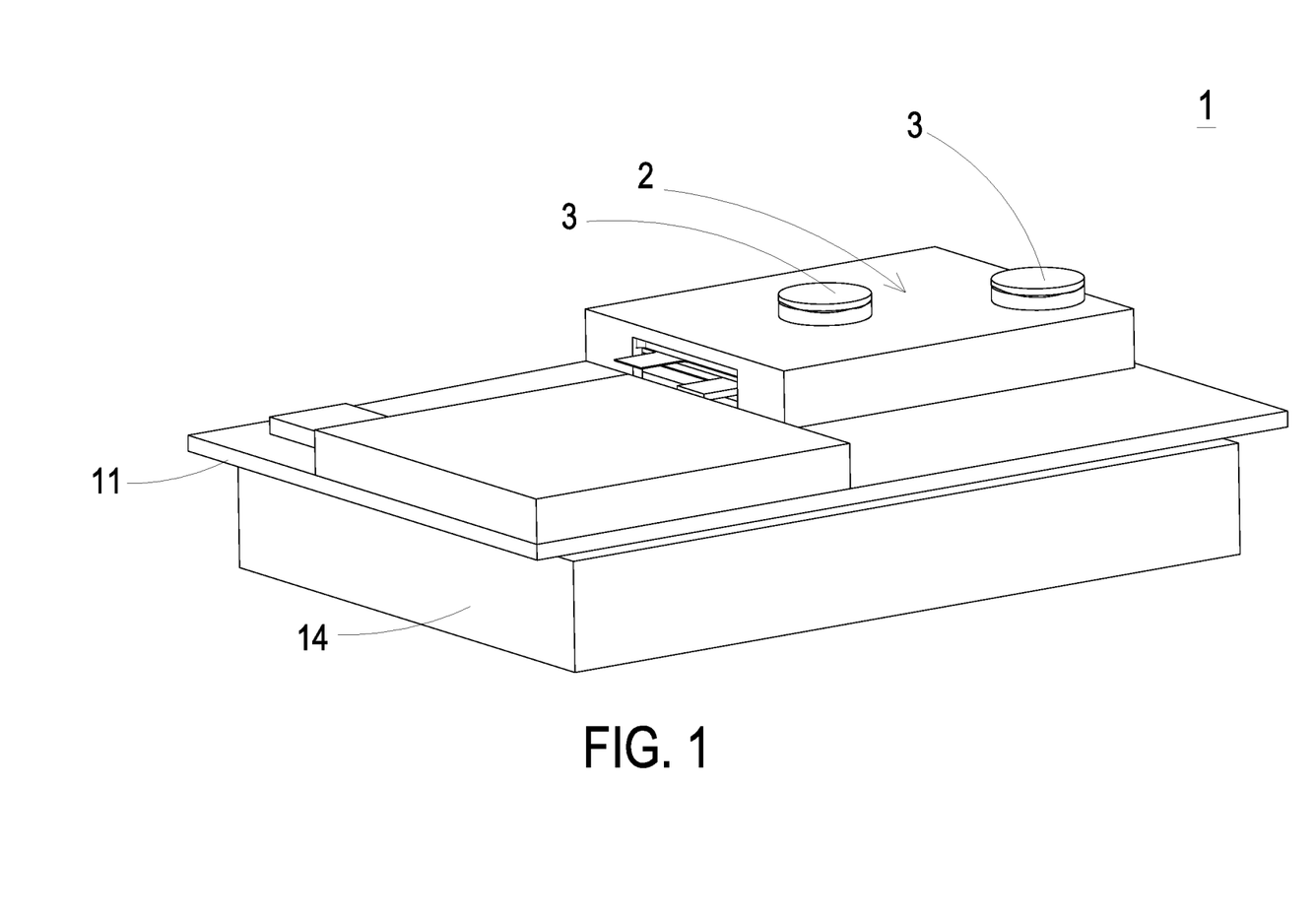
FIG. 1 is a schematic perspective view illustrating an actuating and sensing module according to some embodiments of the present disclosure.
Figure 2A:
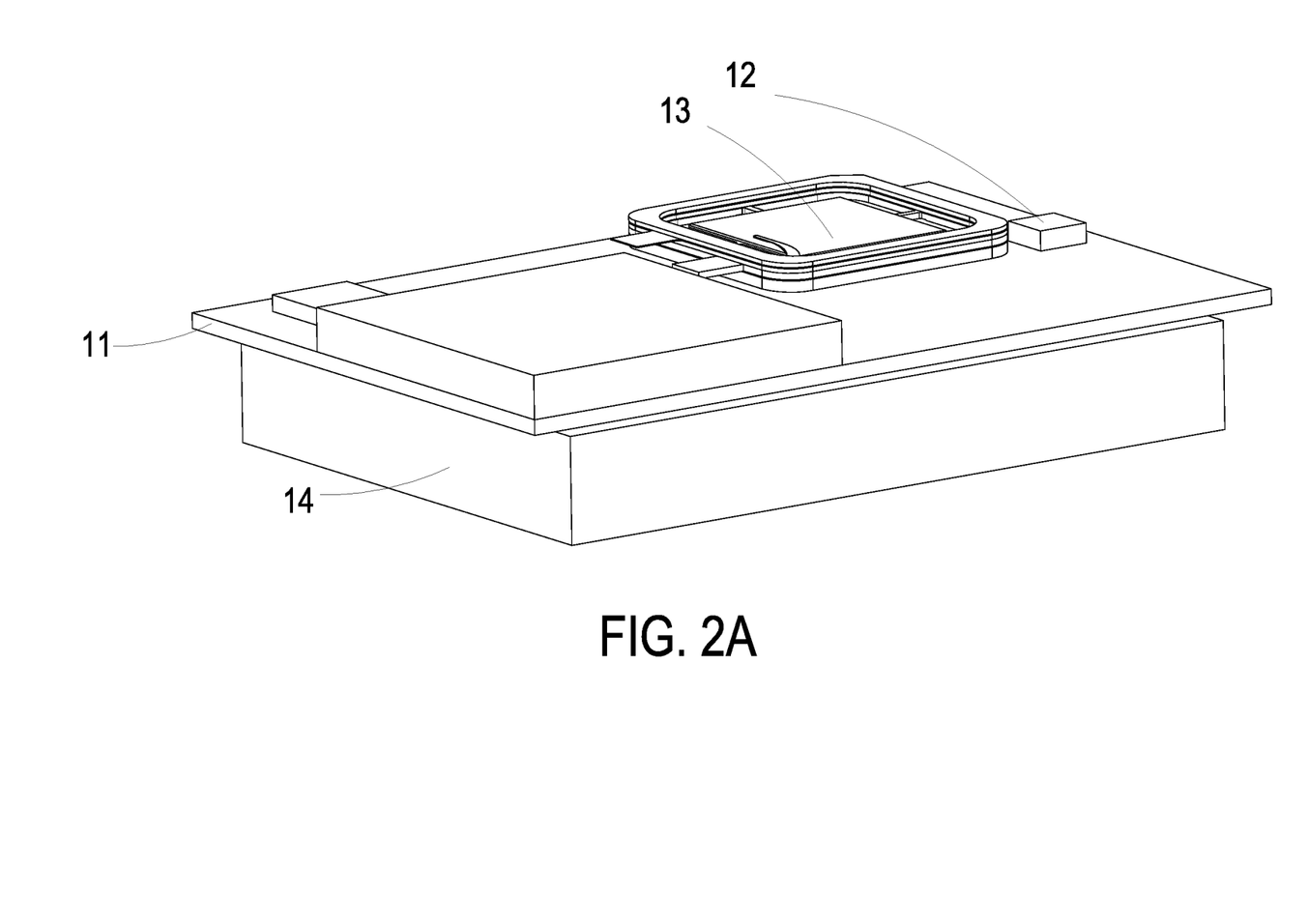
FIG. 2A is a schematic perspective view illustrating an actuating device and a sensor of the actuating and sensing module.

FIG. 1 is a schematic perspective view illustrating an actuating and sensing module according to some embodiments of the present disclosure. FIG. 2A is a schematic perspective view illustrating an actuating device and a sensor of the actuating and sensing module. Referring to FIGS. 1 and 2A, the present discourse provides an actuating and sensing module 1 including at least one sensor 12, at least one actuating device 13, and at least one power storage member 14 configured as at least one graphene battery. The number of the power storage member 14 and the graphene battery is exemplified by one for each in the following embodiments but not limited thereto. It is noted that the power storage member 14 can also be provided in plural numbers.

Figure 2B:
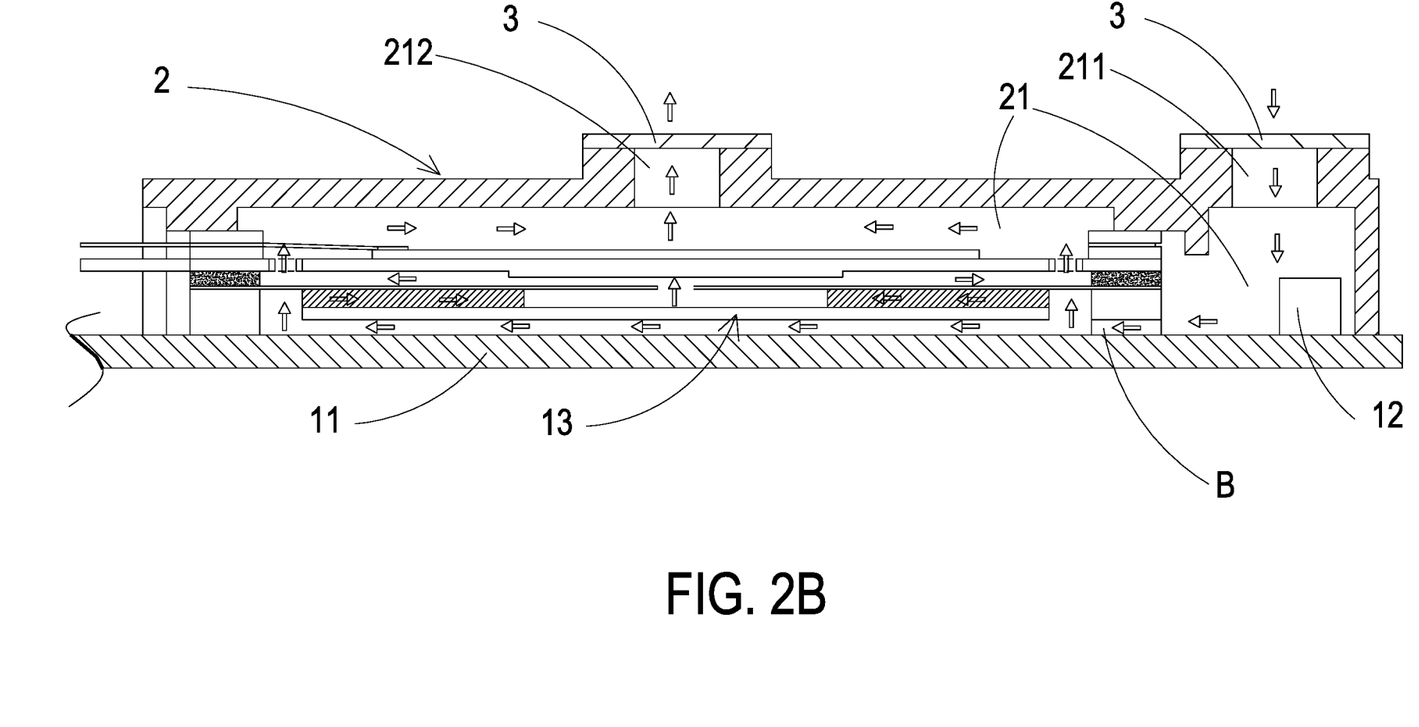
FIG. 2B is a fragmentary schematic cross-sectional view illustrating the actuating and sensing module according to some embodiments of the present disclosure.

FIG. 2B is a fragmentary schematic cross-sectional view illustrating the actuating and sensing module according to some embodiments of the present disclosure. Referring to FIGS. 1, 2A and 2B, the actuating and sensing module 1 includes a sensor 12, an actuating device 13 and a power storage member 14. The sensor 12, the actuating device 13 and the power storage member 14 are integrally disposed on a carrier 11 to be a modularized structure. In some embodiments, the carrier 11 is configured as a substrate such as a printed circuit board (PCB). In some embodiments, an array of the sensor 12 and the actuating device 13 may be disposed on the carrier 11. It is noted that, in some other embodiments, the configuration of the carrier 11 is not restricted, and the carrier 11 may be other platform disposed for supporting and integrating the sensor 12 and the actuating device 13. In some embodiments, the actuating and sensing module 1 has an inhale channel (B) located between the actuating device 13 and the carrier 11.

For achieving the portable purpose of the actuating and sensing module 1, it is necessary to minimize the entire volume of the actuating and sensing module 1 so as to miniaturize the actuating and sensing module 1. In order to achieve the portable purpose for the user, the power storage member 14 should be miniaturized. In some embodiments, the power storage member 14 is configured as a battery made of a graphene doping material to induce the chemical potential energy of the graphene to be converted. By using the power storage member made of graphene material, it can not only increase the carrier density of the graphene (i.e. reduce the impedance of the battery in series), but also increase the internal electric potential of the battery (i.e. increase the turn-on voltage) so as to thin the entire module and achieve the portable purpose of the actuating and sensing module 1. The power storage member 14 outputs and provides driving power to the sensor 12 and the actuating device 13 for driving the sensor 12 and the actuating device 13. The actuating device 13 is driven to transport fluid to flow toward the sensor 12 so as to make the fluid measured by the sensor 12. In some embodiments, the fluid may be gas or liquid, but not limited thereto.

Referring to FIGS. 2A and 2B, in some embodiments, the actuating and sensing module 1 further includes a main body 2 and the main body 2 has a measuring chamber 21. The sensor 12 and the actuating device 13 are disposed in the measuring chamber 21. The main body 2 has an inlet passage 211 and an outlet passage 212 disposed for allowing the fluid introduced from the inlet passage 211 to the measuring chamber 21 and discharged from the measuring chamber 21 to the outside of the main body 2 through the outlet passage 212. In some embodiments, the fluid is air. The inlet passage 211 and the outlet passage 212 are attachedly and respectively covered by two protective films 3. In some embodiments, the protective films 3 are waterproof and dustproof film structures, and only the gas is permitted to pass through the protective films 3, but not limited thereto. The fluid introduced into the inlet passage 211 and the fluid discharged from the outlet passage 212 can be filtered by the protective films 3 in a waterproof and dustproof manner so as to prevent damages of the components within the measuring chamber 21 caused by vapor or dust accumulation.

In some embodiments, the sensor 12 is aligned with the inlet passage 211, and the actuating device 13 is aligned with the outlet passage 212. Moreover, the actuating device 13 is disposed at one side of the sensor 12. After the actuating device 13 is driven to transport the fluid to flow in a flowing direction indicated by the arrows in FIG. 2B, the inhale channel (B) inhales the fluid for allowing the fluid introduced from the inlet passage 211 toward the sensor 12 and measured by the sensor 12. Accordingly, the configuration of the actuating device 13 may help guide the fluid flow in a desired direction and provide an amount of fluid stably and uniformly for the sensor 12. Since the sensor 12 is provided with the amount of the fluid stably and uniformly, the response time of the sensor to the fluid is greatly reduced and the measuring precision is increased.

The sensor 12 is configured as but is not limited to at least one selected from the group consisting of a temperature sensor, a volatile organic compound sensor (e.g., a sensor for measuring formaldehyde or ammonia gas), a particulate sensor (e.g., a fine suspended particle (PM2.5) sensor), a carbon monoxide sensor, a carbon dioxide sensor, an oxygen sensor, an ozone sensor, any other appropriate gas sensor, a humidity sensor, a water content sensor, a substance sensor (e.g., a sensor for measuring compounds or biological substances in liquid or air), a water quality sensor, any other appropriate liquid sensor, a light sensor, and a combination thereof. Alternatively, the sensor 12 may be configured as at least one selected from the group consisting of a bacterial sensor, a virus sensor, a microorganism sensor, and a combination thereof. In some embodiments, the sensor 12 is configured as a graphene sensor for measuring biomarker and for measuring the concentration of nitrite contained in a breath exhaled by human.

In addition, the actuating device 13 is configured as a driving device capable of driving a desired system in response to a control signal. In some embodiments, the actuating device 13 is configured as but is not limited to at least one selected from the group consisting of an electric actuating device, a magnetic actuating device, a thermal actuating device, a piezoelectric actuating device, a fluid actuating device, and a combination thereof. For example, the electric actuating device may be a DC motor, an AC motor or a step motor, the magnetic actuating device may be a magnetic coil motor, the thermal actuating device may be a heat pump, the piezoelectric actuating device may be a piezoelectric pump, and the fluid actuating device may be a gas pump or a liquid pump.

In some embodiments, the actuating device 13 of the actuating the sensing module 1 is configured as a fluid actuating device. In some embodiments, the actuating device 13 may be a piezoelectric actuating pump or a micro-electromechanical system (MEMS) pump. Hereinafter, the actuations of the actuating device 13 will be described as the piezoelectric actuating pump as follows.

Figure 3A:
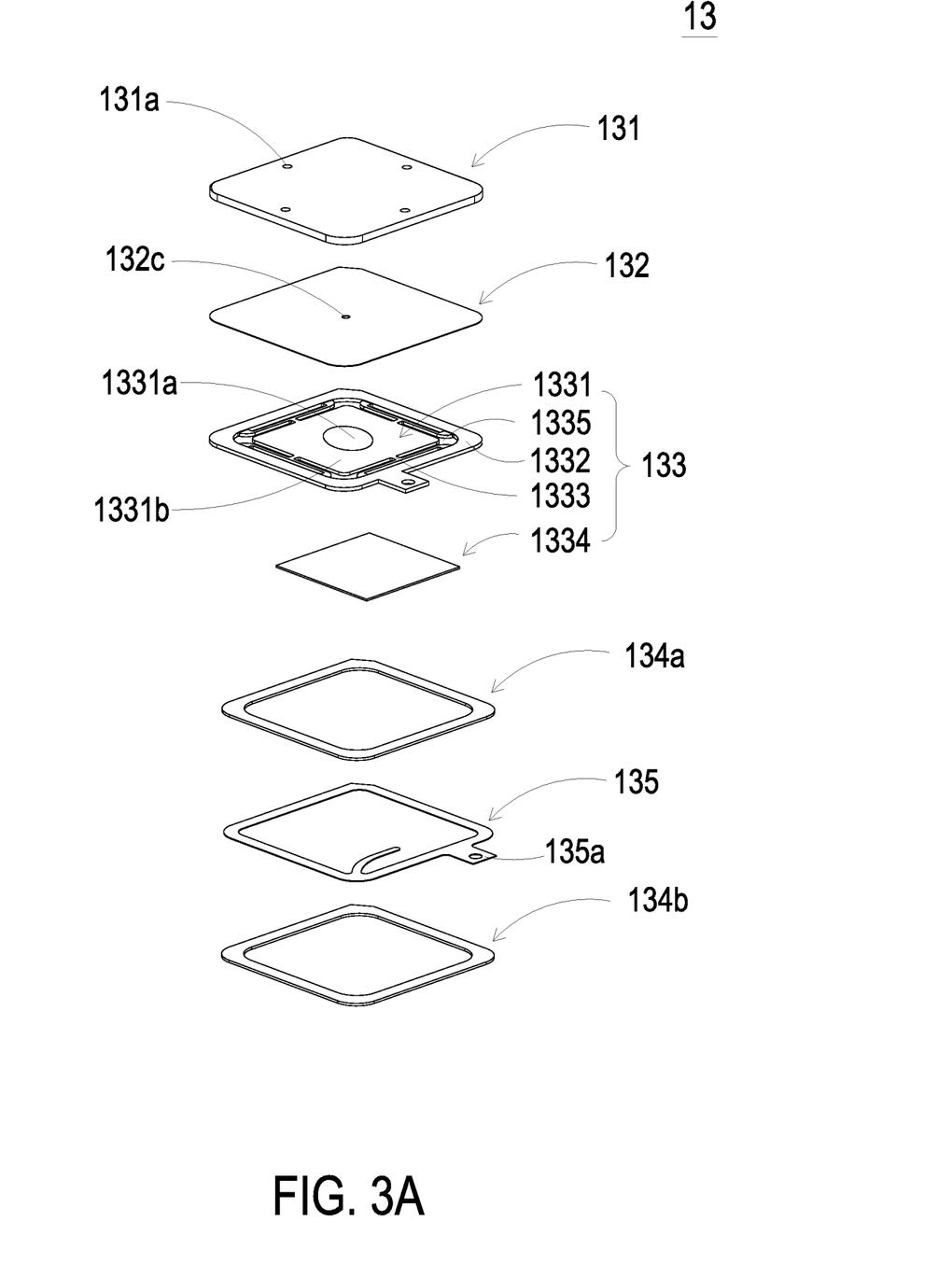
FIG. 3A is a schematic perspective exploded view illustrating the actuating device of the actuating and sensing module.
Figure 3B:
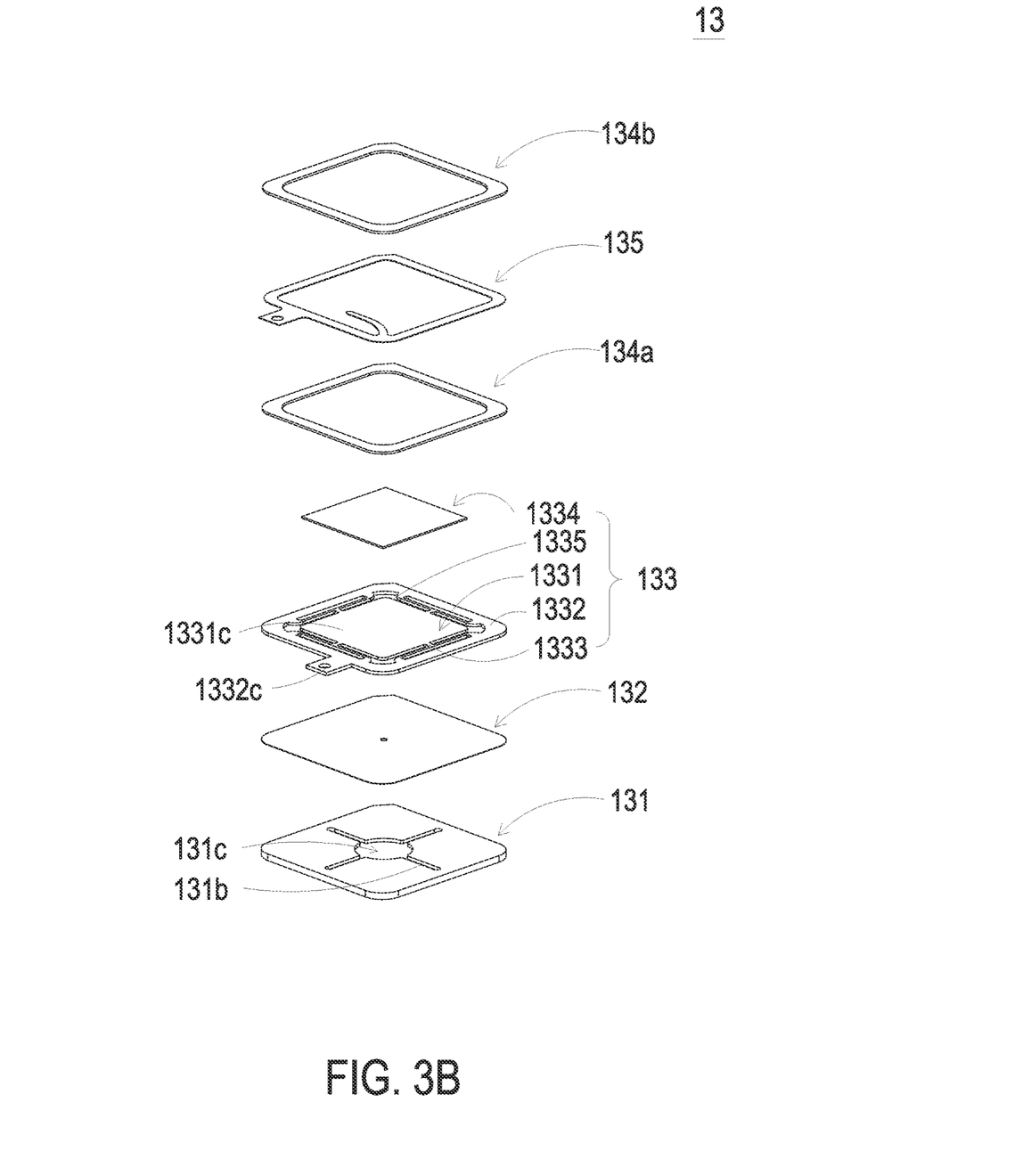
FIG. 3B is another schematic perspective exploded view illustrating the actuating device of the actuating and sensing module.

FIG. 3A is a schematic perspective exploded view illustrating the actuating device of the actuating and sensing module. FIG. 3B is another schematic perspective exploded view illustrating the actuating device of the actuating and sensing module. Referring to FIGS. 2B, 3A and 3B, the actuating device 13 includes a fluid inlet plate 131, a resonance plate 132, a piezoelectric actuator 133, a first insulation plate 134a, a conducting plate 135 and a second insulation plate 134b. The piezoelectric actuator 133 is aligned with the resonance plate 132. The fluid inlet plate 131, the resonance plate 132, the piezoelectric actuator 133, the first insulation plate 134a, the conducting plate 135 and the second insulation plate 134b are stacked on each other sequentially.

In some embodiments, the fluid inlet plate 131 has at least one fluid inlet hole 131a. Preferably but not exclusively, the fluid inlet plate 131 has four fluid inlet holes 131a. The fluid inlet holes 131a extend through the fluid inlet plate 131. In response to the action of the atmospheric pressure, the fluid can be introduced into the actuating device 13 through the at least one fluid inlet hole 131a. Moreover, at least one convergence channel 131b is formed in a surface of the fluid inlet plate 131, and is disposed corresponding in position to the at least one fluid inlet hole 131a, which is formed in another surface of the fluid inlet plate 131. Preferably but not exclusively, the fluid inlet plate 131 has four convergence channels 131b respectively corresponding in position to the fluid inlet holes 131a. Moreover, a central cavity 131c is formed at an intersection of the convergence channels 131b. The central cavity 131c is in communication with the at least one convergence channel 131b, such that the fluid introduced from the at least one fluid inlet hole 131a can be guided to the central cavity 131c through the at least one convergence channel 131b. Consequently, the fluid can be transported fluently. In some embodiments, the at least one fluid inlet hole 131a, the at least one convergence channel 131b and the central cavity 131c of the fluid inlet plate 131 are integrally formed from a single structure. The central cavity 131c is configured as a convergence chamber disposed for temporarily storing the fluid. In some embodiments, the fluid inlet plate 131 is, for example, made of stainless steel. Moreover, the depth of the convergence chamber defined by the central cavity 131c is equal to the depth of the at least one convergence channel 131b, but not limited thereto. In some embodiments, the resonance plate 132 is made of a flexible material, but not limited thereto. The resonance plate 132 has a central aperture 132c corresponding in position to the central cavity 131c of the fluid inlet plate 131, so as to allow the fluid to flow therethrough. In some other embodiments, the resonance plate 132 may be, for example, made of copper, but not limited thereto.

The piezoelectric actuator 133 has a suspension plate 1331 having a first surface 1331b and a second surface 1331c that is opposite to the first surface 1331b, an outer frame 1332, at least one bracket 1333 and a piezoelectric plate 1334. The piezoelectric plate 1334 is attached on the second surface 1331c of the suspension plate 1331. In response to an applied voltage, the piezoelectric plate 1334 would be subjected to a deformation. When the piezoelectric plate 1334 is subjected to the deformation, it facilitates a bending vibration of the suspension plate 1331. In some embodiments, the at least one bracket 1333 is connected between the suspension plate 1331 and the outer frame 1332, while two ends of the at least one bracket 1333 are respectively connected to the outer frame 1332 and the suspension plate 1331 for providing an elastically support. At least one interspace 1335 is formed among the at least one bracket 1333, the suspension plate 1331 and the outer frame 1332. The at least one interspace 1335 is in communication with the measuring chamber 21 for allowing the fluid to flow through. It has to be emphasized that the type and the number of the suspension plate 1331, the outer frame 1332 and the at least one bracket 1333 may be varied according to the practical requirements. The outer frame 1332 surrounds the suspension plate 1331. Moreover, a frame conducting pin 1332c protrudes outwardly from the outer frame 1332 for being connected to the driving power, but the present disclosure is not limited thereto.

Figure 4:
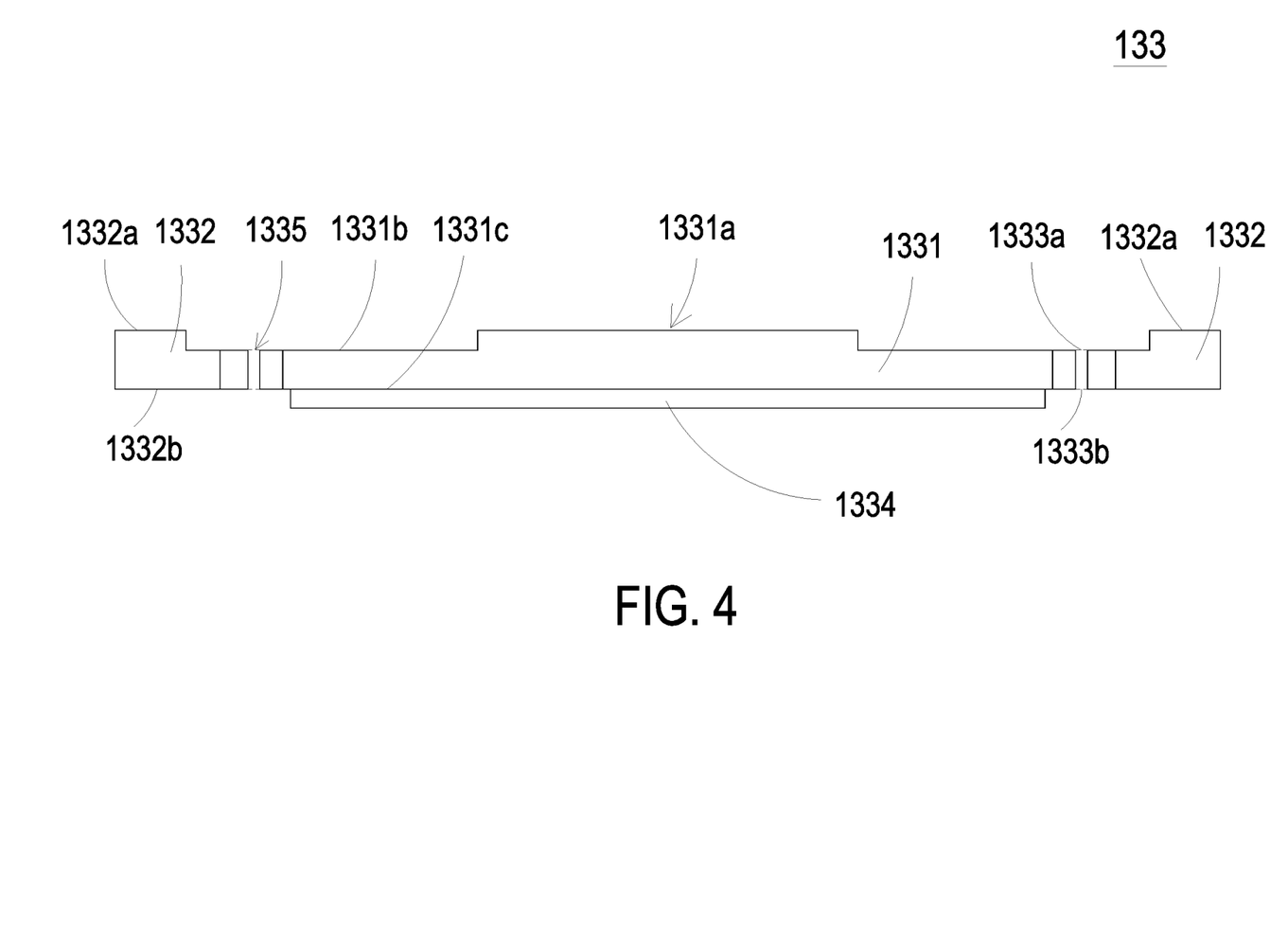
FIG. 4 is a side schematic view illustrating a piezoelectric actuator of the actuating device of the actuating and sensing module.

FIG. 4 is a side schematic view illustrating a piezoelectric actuator of the actuating device of the actuating and sensing module. As shown in FIG. 4, the suspension plate 1331 further has a bulge 1331a that makes the suspension plate 1331 a stepped structure. The bulge 1331a is formed on the first surface 1331b of the suspension plate 1331. In some embodiments, the bulge 1331a is, for example, but not limited to a circular convex structure. The outer frame 1332 has a first surface 1332a and a second surface 1332b opposite to the first surface 1332a. The at least one bracket 1333 has a first surface 1333a and a second surface 1333b opposite to the first surface 1333a. A surface of the bulge 1331a of the suspension plate 1331 that is away from the second surface 1331c of the suspension plate 1331 is coplanar with the first surface 1332a of the outer frame 1332. The first surface 1331b of the suspension plate 1331 is coplanar with the first surface 1333a of the at least one bracket 1333. Moreover, a specified distance is defined from the bulge 1331a of the suspension plate 1331 and the first surface 1332a of the outer frame 1332 to the first surface 1331b of the suspension plate 1331 and the first surface 1333a of the at least one bracket 1333. The second surface 1331c of the suspension plate 1331, the second surface 1332b of the outer frame 1332 and the second surface 1333b of the at least one bracket 1333 are coplanar with each other. In some other embodiments, the suspension plate 1331 may be a square plate structure with two flat surfaces, but the type of the suspension plate 1331 may be varied according to the practical requirements. In some embodiments, the suspension plate 1331, the at least bracket 1333 and the outer frame 1332 may be integrally formed from a metal plate, which can be for example, but not limited to a stainless steel material. The piezoelectric plate 1334 has a side. In some other embodiments, a length of the side of the piezoelectric plate 1334 may be smaller than that of the suspension plate 1331. In some other embodiments, the length of the side of the piezoelectric plate 1334 may be equal to that of the suspension plate 1331. Similarly, the piezoelectric plate 1334 is a square plate structure corresponding in shape to the suspension plate 1331 in terms of the design.

Referring back to FIG. 3A, in some embodiments, the first insulation plate 134a, the conducting plate 135 and the second insulation plate 134b are stacked on each other sequentially at a side of the piezoelectric actuator 133 that is distal from the resonance plate 132. The profiles of the first insulation plate 134a, the conducting plate 135 and the second insulation plate 134b substantially match the profile of the outer frame 1332 of the piezoelectric actuator 133. In some embodiments, the first insulation plate 134a and the second insulation plate 134b are made of an insulating material, for example, but not limited to a plastic material, so as to provide insulating efficacy. In some other embodiments, the conducting plate 135 may be made of an electrically conductive material, for example, but not limited to a metallic material, so as to provide electrically conducting efficacy. In some embodiments, the conducting plate 135 has a plate conducting pin 135a disposed for being connected to the driving power.

Figure 5:
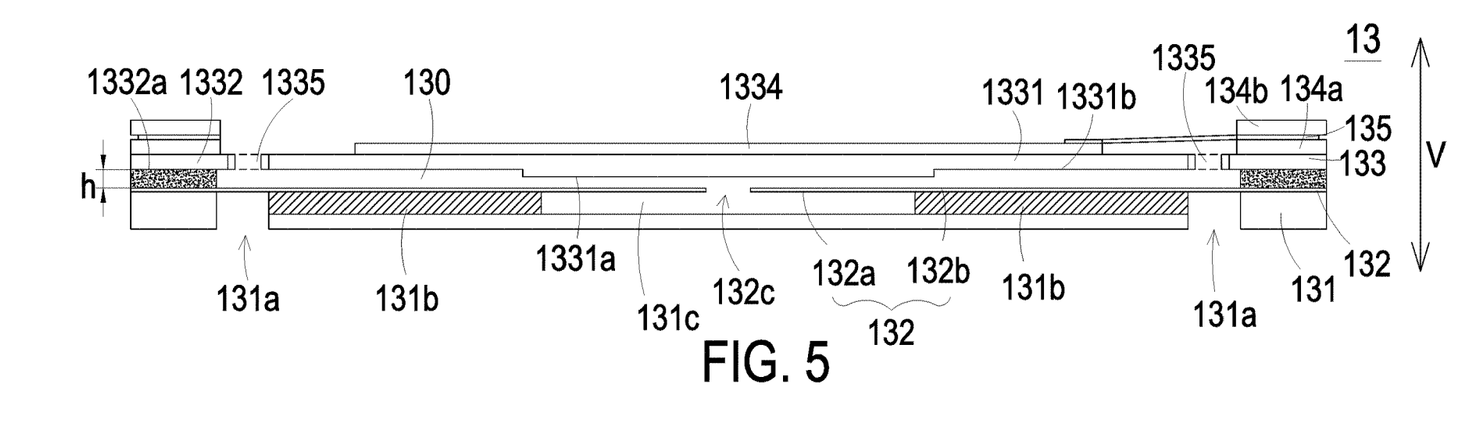
FIG. 5 is a schematic cross-sectional view illustrating the actuating device of the actuating and sensing module.

FIG. 5 is a schematic cross-sectional view illustrating the actuating device of the actuating and sensing module. Referring to FIG. 5, in some embodiments, a gap (h) is formed between the resonance plate 132 and the outer frame 1332 of the piezoelectric actuator 133. In some embodiments, the gap (h) between the resonance plate 132 and the outer frame 1332 of the piezoelectric actuator 133 is filled with a filler, for example, but not limited to a conductive adhesive, so that a depth from the resonance plate 132 to the bulge 1331a of the suspension plate 1331 of the piezoelectric actuator 133 can be maintained. The gap (h) ensures the proper distance between the resonance plate 132 and the bulge 1331a of the suspension plate 1331 of the piezoelectric actuator 133, so that the fluid can be transported rapidly, and the contact interference is reduced so as to greatly reduce the generated noise. In some other embodiments, a thickness of the outer frame 1332 of the piezoelectric actuator 133 in a vibration direction (V) is increased so as to form the gap between the resonance plate 132 and the piezoelectric actuator 133, but the present disclosure is not limited thereto.

Referring to FIGS. 2B, 3A, 3B and 5, in some embodiments, the resonance plate 132 has a movable part 132a and a fixed part 132b. The convergence chamber is collaboratively defined by the movable part 132a of the resonance plate 132 and the fluid inlet plate 131. Moreover, a first chamber 130 is formed between the resonance plate 132 and the piezoelectric actuator 133 for temporarily storing the fluid. The first chamber 130 is in communication with the convergence chamber through the central aperture 132c of the resonance plate 132. A peripheral region of the first chamber 130 is in communication with the measuring chamber 21 through the interspace 1335 between the brackets 1333 of the piezoelectric actuator 133.

Figure 6A:
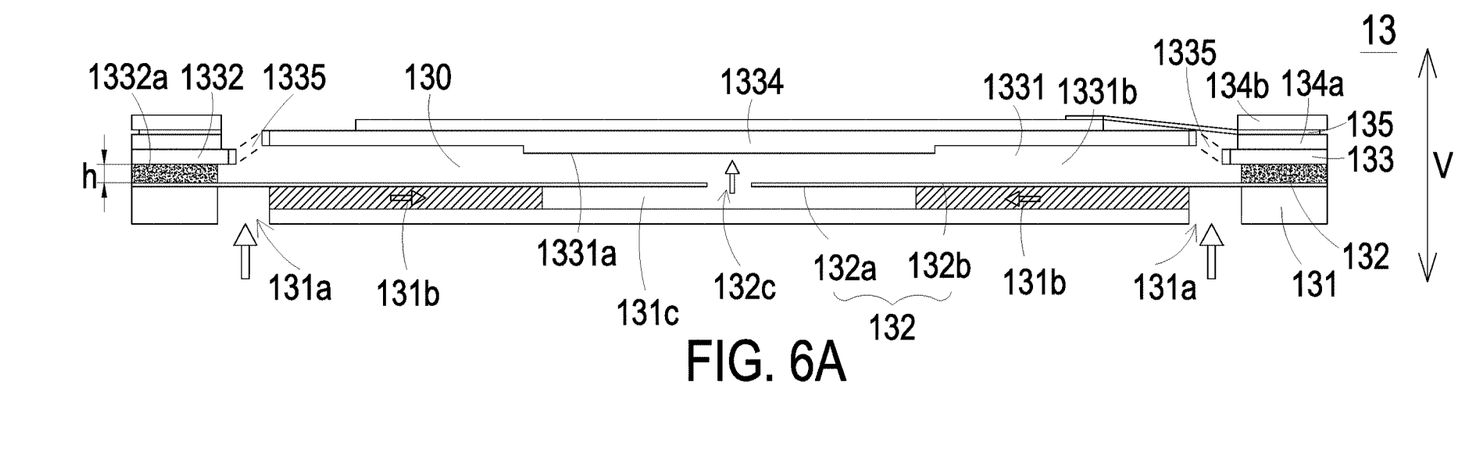
FIGS. 6A to 6E are schematic diagrams illustrating the actuations of the actuating device of the actuating and sensing module.
Figure 6B:
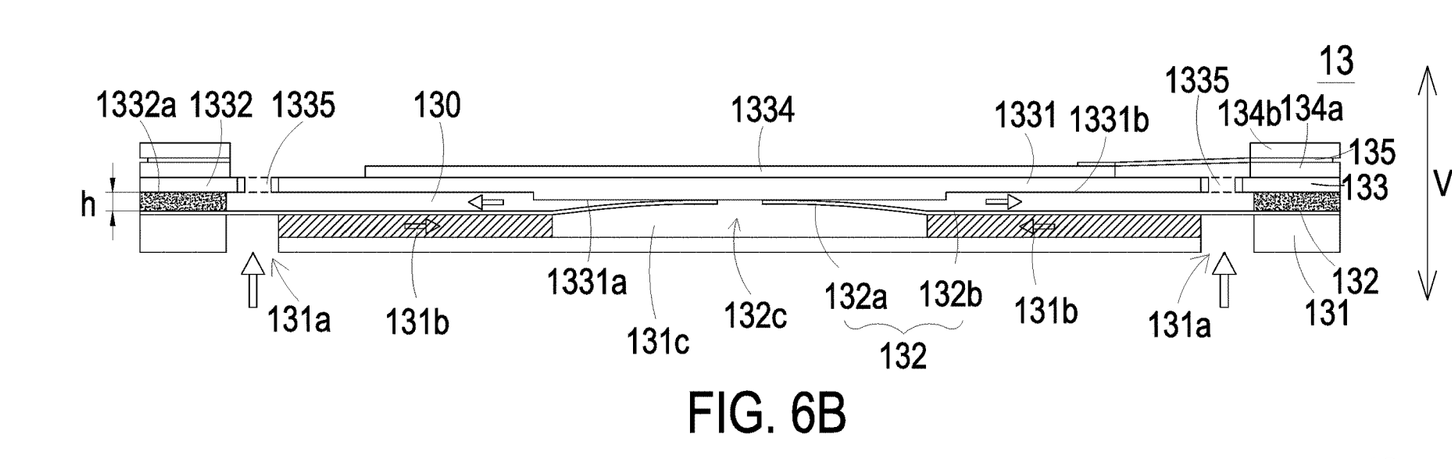
Figure 6C:
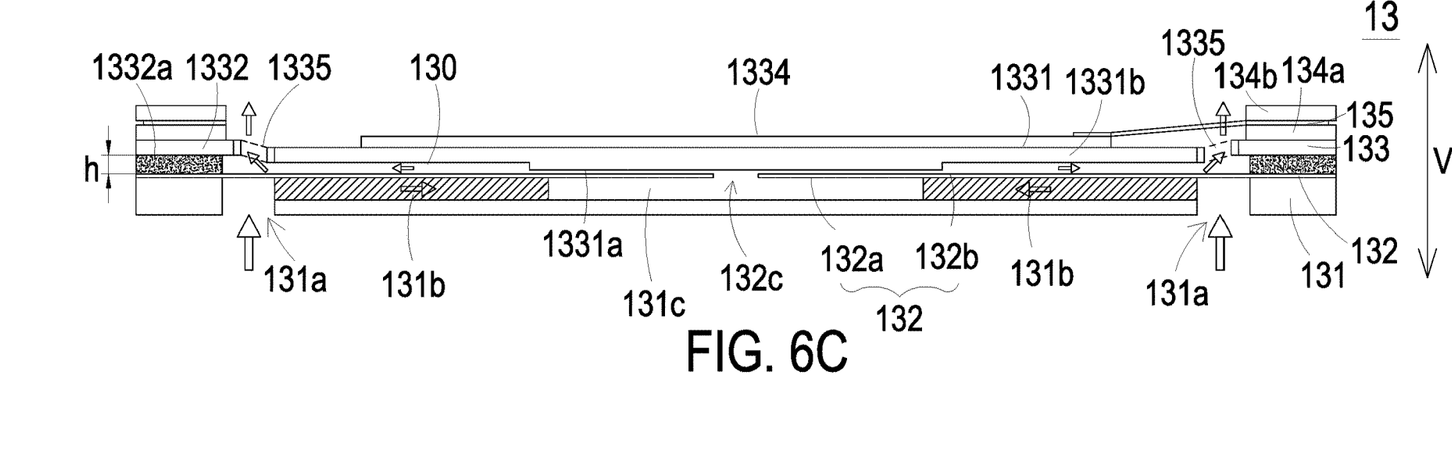
Figure 6D:
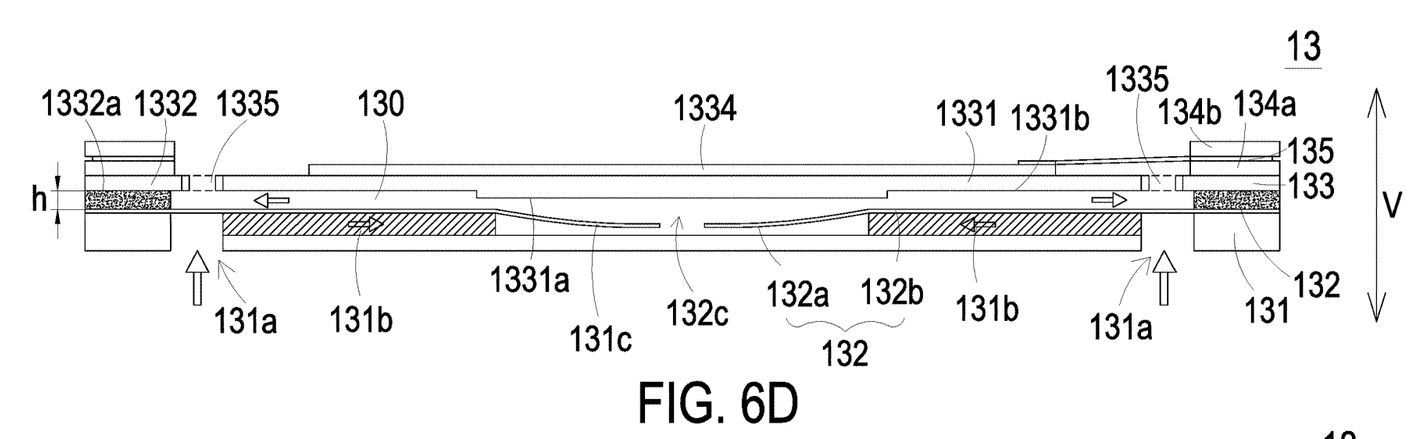
Figure 6E:
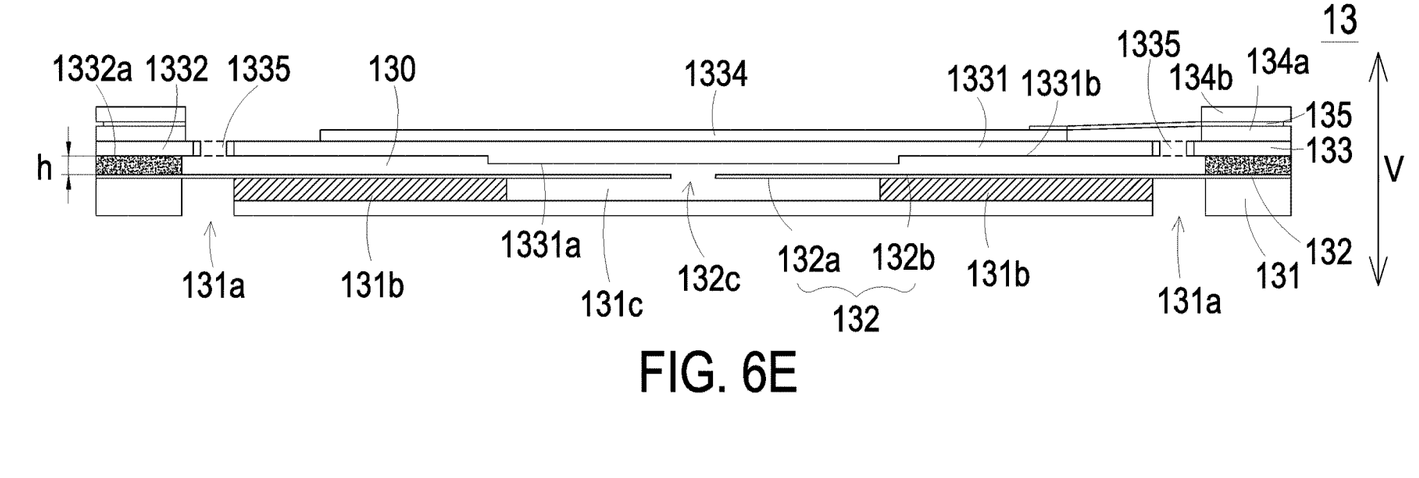

FIGS. 6A to 6E are schematic diagrams illustrating the actuations of the actuating device of the actuating and sensing module. Referring to FIGS. 3A, 3B, 5 and 6A to 6E, the actuations of the actuating device 13 will be described as follows. When the actuating device 13 is driven, the piezoelectric actuator 133 vibrates in the vertical direction (V) in a reciprocating manner by using the bracket 1333 as a fulcrum. As shown in FIG. 6A, the piezoelectric actuator 133 vibrates away from the resonance plate 132 in response to the applied voltage. Since the resonance plate 132 is light and thin, the resonance plate 132 also vibrates in the vertical direction (V) in resonance with the piezoelectric actuator 133. More especially, a region of the resonance plate 132 corresponding in position to the central cavity 131c of the fluid inlet plate 131 is also subjected to a bending deformation. In some embodiments, the region of the resonance plate 132 corresponding in position to the central cavity 131c of the fluid inlet plate 131 is the movable part 132a of the resonance plate 132. When the piezoelectric actuator 133 vibrates away from the resonance plate 132, the movable part 132a of the resonance plate 132 is subjected to the bending deformation because the movable part 132a of the resonance plate 132 is pushed by the fluid and vibrates in response to the piezoelectric actuator 133. In response to the vibration of the piezoelectric actuator 133, the fluid is inhaled into the at least one fluid inlet hole 131a of the fluid inlet plate 131. Then, the fluid is transported to the central cavity 131c of the fluid inlet plate 131 through the at least one convergence channel 131b. Next, the fluid is transported through the central aperture 132c of the resonance plate 132, and introduced into the first chamber 130. As the piezoelectric actuator 133 is driven, the resonance of the resonance plate 132 occurs. Consequently, the resonance plate 132 vibrates in the vertical direction (V) in the reciprocating manner. As shown in FIG. 6B, during the vibration of the movable part 132a of the resonance plate 132, the movable part 132a of the resonance plate 132 moves toward the suspension plate 1331 and comes into contact with the bulge 1331a of the suspension plate 1331 of the piezoelectric actuator 133. A distance from the fixed part 132b of the resonance plate 132 to a region of the suspension plate 1331 that excludes the bulge 1331a remains the same. Owing to the deformation of the resonance plate 132 described above, the volume of the first chamber 130 is compressed and the convergence chamber is no longer in communication with the first chamber 130. Under this circumstance, a pressure gradient occurs to push the fluid in the first chamber 130 to move toward the peripheral region of the first chamber 130 and to be further transported through the interspace 1335 of the piezoelectric actuator 133. As shown in FIG. 6C, the movable part 132a of the resonance plate 132 returns to its initial position when the piezoelectric actuator 133 vibrates toward the resonance plate 132. Consequently, the volume of the first chamber 130 is continuously compressed to generate the pressure gradient which makes the fluid in the first chamber 130 continuously moved toward the peripheral region. Meanwhile, the fluid is continuously inhaled into the at least one fluid inlet hole 131a of the fluid inlet plate 131, and is transported to the central cavity 131c. Subsequently, as shown in FIG. 6D, the resonance plate 132 moves toward the fluid inlet plate 131, which is cause by the resonance of the piezoelectric actuator 133. That is, the movable part 132a of the resonance plate 132 also vibrates toward the fluid inlet plate 131 in resonance with the piezoelectric actuator 133. Consequently, the fluid inhaled from the at least one fluid inlet hole 131a of the fluid inlet plate 131 and into the central cavity 131c is decreased. At last, as shown in FIG. 6E, the movable part 132a of the resonance plate 132 returns to its initial position. As the embodiments described above, when the resonance plate 132 vibrates in the vertical direction (V) in the reciprocating manner, the gap (h) between the resonance plate 132 and the piezoelectric actuator 133 is helpful to increase the maximum displacement in the vertical direction (V) during the vibration of the resonance plate 132. In other words, the disposition of the gap (h) between the resonance plate 132 and the piezoelectric actuator 133 can increase the amplitude of vibration of the resonance plate 132. Consequently, the pressure gradient is generated to facilitate the fluid to flow at a high speed. Moreover, since there is an impedance difference between the inhaling direction and the discharging direction, the fluid can be transported from an inlet end to an outlet end. Even if a gas pressure exists at the outlet end, the actuating device 13 still has the capability to push the fluid into the measuring chamber 21 while achieving the silent efficacy. The steps of FIGS. 6A to 6E may be implemented repeatedly. Consequently, the environmental fluid is transported by the actuating device 13 from the outside to the inside of the actuating and sensing module 1.

The operations of the actuating device 13 are further described as follows. After the actuating device 13 is assembled, the actuating device 13 is mounted in the carrier 11. When the actuating device 13 is driven, the fluid flows in the flowing direction indicated by the arrows (see FIG. 2B). The inhale channel (B) inhales the fluid for allowing the fluid introduced from the inlet passage 211 to flow toward the sensor 12 and to be measured by the sensor 12. Accordingly, the configuration of the actuating device 13 can guide the fluid to flow in a desired direction and provide the amount of fluid stably and uniformly for the sensor 12. Since the sensor 12 is provided with the amount of the fluid stably and uniformly, the response time of the sensor 12 to the fluid is greatly reduced and the measuring precision is improved.

Figure 7:
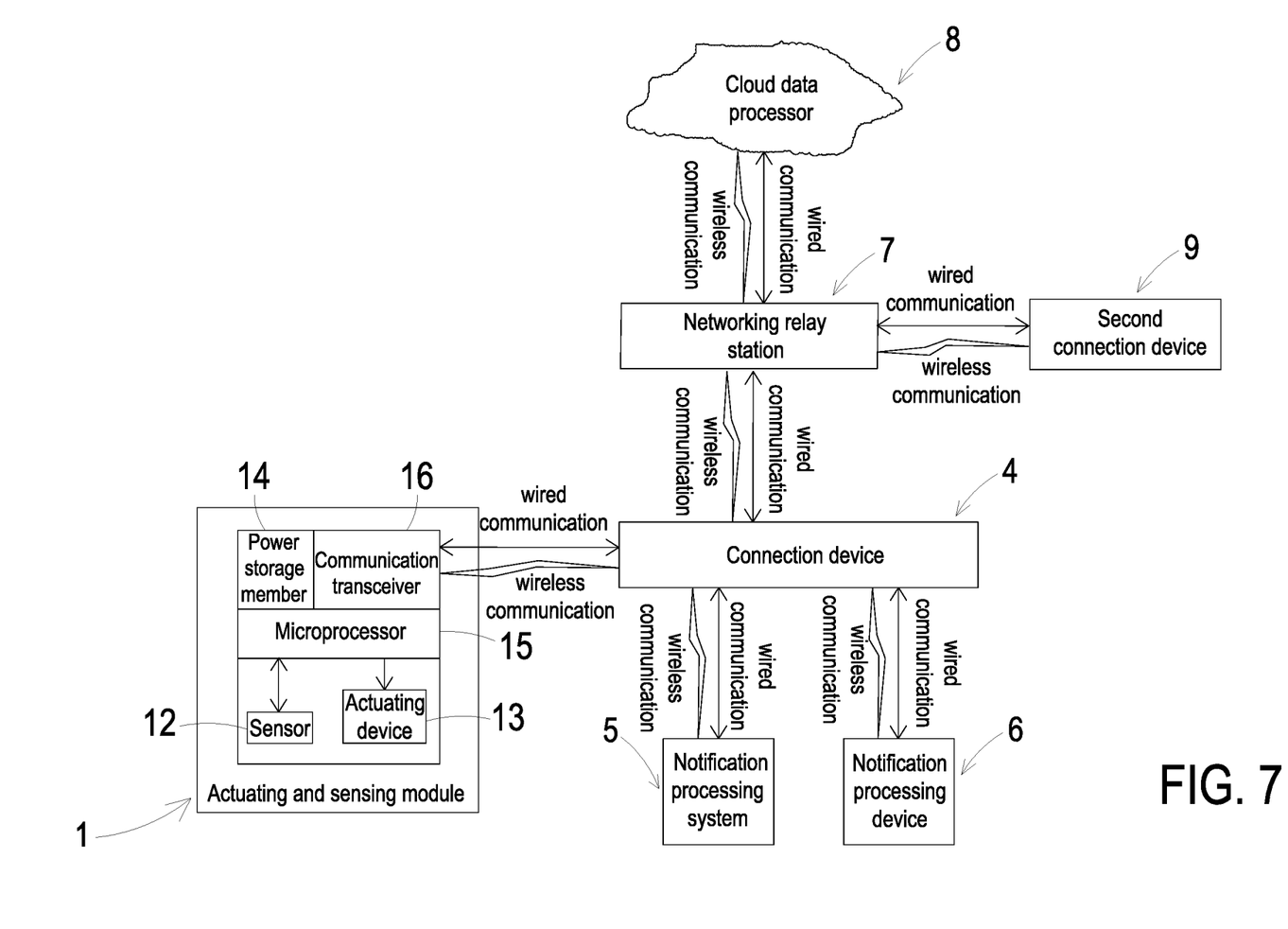
FIG. 7 is a system diagram illustrating a data transmitting system for the actuating and sensing module.

FIG. 7 is a system diagram illustrating a data transmitting system for the actuating and sensing module. Referring to FIG. 7, the power storage member 14 of the actuating and sensing module 1 is disposed for storing and outputting power. The power storage member 14 provides the driving power for the sensor 12 and the actuating device 13 to drive the sensor 12 and the actuating device 13. In some embodiments, the actuating and sensing module 1 further includes a microprocessor 15 and a communication transceiver 16. The sensor 12 is disposed for measuring the environment to acquire a measured data. The microprocessor 15 processes and calculates the measured data from the sensor 12 and controls the actuating device 13. The communication transceiver 16 is disposed for receiving or transmitting data. The microprocessor 15 receives the measured data from the sensor 12, and processes and converts the measured data into an output data. The communication transceiver 16 then receives the output data from the microprocessor 15 and transmits the output data to a connection device 4. After that, the connection device 4 displays or stores information having the output data, or transmits the information having the output data to a storage device to be stored and processed. In some embodiments, the connection device 4 is connected to a notification processing system 5 to actively (e.g., directly notify) or passively (e.g., in response to the operation by a user who requests the output data) enable an air quality notification mechanism. For example, an instant air quality map informs people to avoid away or wear masks. In some other embodiments, the connection device 4 is connected to a notification processing device 6 to actively (e.g., directly notify) or passively (e.g., in response to the operation by a user who requests the output data) enable an air quality processing mechanism. For example, an air cleaner or an air-conditioner is driven to clean the air.

In some embodiments, the connection device 4 is configured as a display device having a wired communication module (e.g., a desktop computer). In some other embodiments, the connection device 4 is configured as a display device having a wireless communication module (e.g., a notebook computer). In some other embodiments, the connection device 4 is configured as a portable mobile device having a wireless communication module (e.g., a mobile phone). The wired communication module may have an RS485 communication port, an RS232 communication port, a Modbus communication port or a KNX communication port for wired communication. The wireless communication module may perform a wireless communication through a Zigbee communication technology, a Z-wave communication technology, an RF communication technology, a Bluetooth communication technology, a Wifi communication technology or an EnOcean communication technology.

The data transmitting system further includes a networking relay station 7 and a cloud data processor 8. The connection device 4 is disposed for transmitting the output data to the networking relay station 7. Then, the output data is transmitted from the networking relay station 7 to the cloud data processor 8 to be stored and processed. After the output data is processed by the cloud data processor 8, the cloud data processor 8 issues a notification signal to the networking relay station 7. Then, the networking relay station 7 transmits the notification signal to the connection device 4. After receiving the notification signal from the connection device 4, the notification processing system 5 enables an air quality notification mechanism. Alternatively, after receiving the notification signal from the connection device 4, the notification processing device 6 enables an air quality processing mechanism.

In some embodiments, the connection device 4 issues a control command to the actuating and sensing module 1 so as to control the operation of the actuating and sensing module 1. In other words, the control command may be transmitted to the communication transceiver 16 through wired communication or wireless communication. Then, the control command is transmitted to the microprocessor 15 to control the sensor 12 and the actuating device 13 to perform the measuring operation and the operation of the actuating device 13.

In some embodiments, the data transmitting system further includes a second connection device 9 disposed for issuing a control signal. After the second connection device 9 issues and transmits the control command to the cloud data processor 8 through the networking relay station 7, the control command is transmitted from the cloud data processor 8 to the connection device 4 through the networking relay station 7, so that the connection device 4 transmits the control command to the communication transceiver 16. Subsequently, the control command is transmitted to the microprocessor 15 to control the sensor 12 to perform the measuring operation and to drive the operation of the actuating device 13. In some embodiments, the second connection device 9 is configured as a device having a wired communication module. In some other embodiments, the second connection device 9 is configured as a device having a wireless communication module. In some other embodiments, the second connection device 9 is configured as a portable electronic device having a wireless communication module, but not limited thereto.

From the above descriptions, the present disclosure provides an actuating and sensing module for monitoring the environment, thereby a portable device is provided to monitor the air quality. The actuating device is disposed for increasing the flow rate of fluid and providing the amount of fluid stably and uniformly. Since the sensor is provided with the amount of the fluid stably and uniformly, the response time of the sensor to the fluid is greatly reduced and the measuring precision is improved. Moreover, after a measured data is provided by the actuating and sensing module and processed into an output data, the output data is transmitted to the connection device. The output data is then displayed, stored and transmitted by the connection device. Consequently, the purpose of immediately displaying the output data and issuing the notification signal are achieved. Moreover, the output data can be transmitted to a cloud database. Consequently, the purpose of constructing and managing the cloud database can be achieved. Accordingly, an air quality notification mechanism and an air quality processing mechanism are enabled to remove the pollutants in the air. In other words, the device of the present disclosure is industrially valuable.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An actuating and sensing module, comprising:
   at least one sensor disposed for measuring fluid;
   at least one actuating device configured as a fluid actuating device, wherein the fluid actuating device is a piezoelectric pump, wherein the piezoelectric pump comprises a fluid inlet plate, a resonance plate, a piezoelectric actuator, a first insulation plate, a conducting plate and a second insulation plate, wherein the fluid inlet plate, the resonance plate, the piezoelectric actuator, the first insulation plate, the conducting plate and the second insulation plate are stacked on each other sequentially, wherein the at least one actuating device is disposed proximate to the at least one sensor and disposed for transporting the fluid;
a power storage member configured as a graphene battery, and disposed for providing power to the at least one sensor and the at least one actuating device for driving the at least one sensor and the at least one actuating device;
a carrier configured as a substrate, wherein the at least one sensor, the at least one actuating device and the power storage member are integrally disposed on the carrier to be a modularized structure;
a main body having a measuring chamber, wherein the at least one sensor and the at least one actuating device are disposed in the measuring chamber; and
an inhale channel disposed in the measuring chamber;
wherein when the at least one actuating device is driven, the inhale channel inhales the fluid for allowing the fluid to be introduced toward the at least one sensor, so as to make the fluid measured by the at least one sensor.

2. The actuating and sensing module according to claim 1, wherein:
the main body has an inlet passage and an outlet passage disposed for allowing the fluid introduced from the inlet passage into the measuring chamber and discharged from the measuring chamber to outside of the main body through the outlet passage; and
the sensor is aligned with the inlet passage, and the actuating device is aligned with the outlet passage.

3. The actuating and sensing module according to claim 1, wherein the sensor is configured as at least one selected from the group consisting of a gas sensor, an oxygen sensor, a carbon monoxide sensor, a carbon dioxide sensor, a liquid sensor, a temperature sensor, a humidity sensor, an ozone sensor, a particulate sensor, a volatile organic compound sensor, a light sensor, and combinations thereof.

4. The actuating and sensing module according to claim 1, wherein the sensor is configured as a graphene sensor.

5. The actuating and sensing module according to claim 1, wherein the sensor is configured as at least one selected from the group consisting of a bacterial sensor, a virus sensor, a microorganism sensor, and combinations thereof.

6. The actuating and sensing module according to claim 1, wherein the sensor is configured as a sensor for measuring a biomarker.

7. The actuating and sensing module according to claim 1, wherein the fluid inlet plate has at least one fluid inlet hole, at least one convergence channel and a central cavity, wherein the central cavity defines convergence chamber, wherein the at least one fluid inlet hole is disposed for introducing the fluid, wherein the convergence channel is disposed corresponding in position to the fluid inlet hole for guiding the fluid from the fluid inlet hole toward the convergence chamber; wherein the resonance plate has a central aperture and a movable part, wherein the central aperture is aligned with the convergence chamber and the movable part surrounds the central aperture; and wherein the piezoelectric actuator is aligned with the resonance plate, wherein a gap is formed between the resonance plate and the piezoelectric actuator and is defined as a first chamber, so that when the piezoelectric actuator is driven, the fluid introduced from the at least one fluid inlet hole of the fluid inlet plate is converged to the central cavity through the at least one convergence channel, and flows into the first chamber through the central aperture of the resonance plate, whereby the fluid is further transported via a resonance between the piezoelectric actuator and the movable part of the resonance plate.

8. The actuating and sensing module according to claim 7, wherein the piezoelectric actuator includes:
a suspension plate being square-shaped and having a first surface, a second surface opposite to the first surface and a bulge, wherein the suspension plate is permitted to undergo a bending vibration;
an outer frame surrounding the suspension plate; at least one bracket connected between the suspension plate and the outer frame for providing an elastic support; and
a piezoelectric plate having a side, wherein a length of the side of the piezoelectric plate is less than or equal to that of the suspension plate, and the piezoelectric plate is attached on the second surface of the suspension plate, and wherein when a voltage is applied to the piezoelectric plate, the suspension plate is driven to undergo the bending vibration.

9. The actuating and sensing module according to claim 1, further comprising:
a microprocessor configured to process and calculate a data measured by the sensor, and drive the actuating device, wherein the data measured by the sensor is processed into an output data by the microprocessor; and
a communication transceiver configured to receive and transmit data signal, wherein the communication transceiver receives the output data from the microprocessor and transmits the output data to a connection device, and wherein the connection device displays, stores and transmits the output data,
wherein the connection device is configured as a portable mobile device having a wireless communication module, and wherein the output data is transmitted from the connection device to a networking relay station, and is then transmitted from the networking relay station to a cloud data processor, so that the output data is processed by and stored in the cloud data processor.

10. The actuating and sensing module according to claim 9, wherein the connection device is connected to one of a notification processing system and a notification processing device so as to enable an air quality notification mechanism.

11. The actuating and sensing module according to claim 9, wherein the connection device is configured as one of a display device having a wired communication module and a display device having a wireless communication module.

12. The actuating and sensing module according to claim 9, wherein the cloud data processor issues a notification signal after processing the output data, the notification signal is transmitted to the networking relay station and is then transmitted to the connection device, and wherein the connection device is connected to a notification processing system for enabling an air quality notification mechanism.

13. The actuating and sensing module according to claim 9, wherein the cloud data processor issues a notification signal after processing the output data, the notification signal is transmitted to the networking relay station and is then transmitted to the connection device, and wherein the connection device is connected to a notification processing device for enabling an air quality processing mechanism.

14. The actuating and sensing module according to claim 9, further comprising a second connection device disposed for sending a control command, wherein the control command is transmitted from the second connection device to the cloud data processor through the networking relay station, and is then transmitted from the cloud data processor to the connection device through the networking relay station, so that the connection device sends the control command to the communication transceiver of the actuating and sensing module.

15. The actuating and sensing module according to claim 14, wherein the second connection device is configured as one of a device having a wired communication module and a device having a wireless communication module.

16. An actuating and sensing module, comprising:
at least one sensor disposed for measuring fluid;
at least one actuating device configured as a fluid actuating device, wherein the fluid actuating device is a piezoelectric pump, wherein the piezoelectric pump comprises a fluid inlet plate, a resonance plate, a piezoelectric actuator, a first insulation plate, a conducting plate and a second insulation plate, wherein the fluid inlet plate, the resonance plate, the piezoelectric actuator, the first insulation plate, the conducting plate and the second insulation plate are stacked on each other sequentially, wherein the at least one actuating device is disposed proximate to the at least one sensor and disposed for transporting the fluid;
at least one power storage member configured as at least one graphene battery, disposed for providing power to the at least one sensor and the at least one actuating device for driving the at least one sensor and the at least one actuating device;
at least one carrier configured as a substrate, wherein the at least one sensor, the at least one actuating device and the at least one power storage member are integrally disposed on the at least one carrier to be a modularized structure;
at least one main body having at least one measuring chamber, wherein the at least one sensor and the at least one actuating device are disposed in the at least one measuring chamber; and
at least one inhale channel disposed in the at least one measuring chamber;
wherein when the at least one actuating device is driven, the at least one inhale channel inhales the fluid for allowing the fluid to be introduced toward the at least one sensor so as to make the fluid measured by the at least one sensor.

* * * * *